Figure 1:
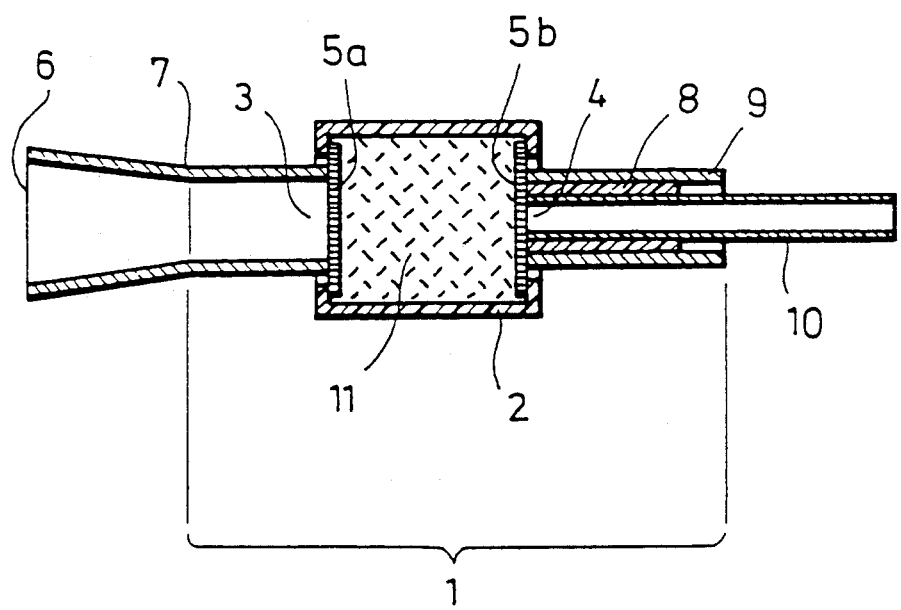

United States Patent [19]

Henco et al.

[11] Patent Number: 5,057,426

[45] Date of Patent: Oct. 15, 1991

[54] METHOD FOR SEPARATING LONG-CHAIN NUCLEIC ACIDS

[75] Inventors: Karsten Henco, Erkrath; Arndt Stichel, Duesseldorf; Metin Colpan, Erkrath, all of Fed. Rep. of Germany

[73] Assignee: DIAGEN Institut fur molekular-biologische, Diagnostik GmbH, Fed. Rep. of Germany

[21] Appl. No.: 123,698

[22] Filed: Nov. 23, 1987

[30] Foreign Application Priority Data

Nov. 22, 1986 [DE] Fed. Rep. of Germany ....... 3639949

[51] Int. Cl.$^5$ ..................... C12N 1/08; C07H 15/12
[52] U.S. Cl. ..................... 435/270; 536/27; 536/28
[58] Field of Search ............ 536/28, 27; 435/270

[56] References Cited

U.S. PATENT DOCUMENTS

| | | | |
|---|---|---|---|
| 3,157,635 | 11/1964 | Tanaka et al. | 536/28 |
| 3,157,636 | 11/1964 | Sanno et al. | 536/28 |
| 3,433,782 | 3/1969 | Kreiser | 536/28 |
| 4,430,496 | 2/1984 | Abbott | 536/27 |
| 4,935,342 | 6/1990 | Seligson et al. | 935/77 |

FOREIGN PATENT DOCUMENTS

| | | |
|---|---|---|
| 0240191 | 10/1987 | European Pat. Off. |
| 1331933 | 9/1973 | United Kingdom ............ 435/270 |

OTHER PUBLICATIONS

Kato et al.-J. of Chromatography, vol. 265, (Aug. 19, 1983), pp. 342-346.
Hecker et al.-J. of Chromatography, vol. 326, Jun. 19, 1985, pp. 251-261.
Patent Abstract of Japan, vol. 11, No. 13 (C-397) [2460], Jan. 14, 1987.
*Pharmacia*, FPLC System, "High Performance Purification of Biomolecules", Sep. 1986, pp. 2-46.
*Pharmacia*, FPLC: Media and Column Guide, "High Performance Separation of Biomolecules", pp. 1-16.
Jandera et al., "Gradient Elution in Column Liquid Chromatography", *Journal of Chromatography Library*, vol. 31, pp. 381-393, 1985.
Mikes, "High-Performance Liquid Chromatography of Biopolymers and Biooligomers", *Journal of Chromatography Library*, vol. 41B, pp. B180-189, B200-211.

*Primary Examiner*—Sam Rosen
*Attorney, Agent, or Firm*—Wegner, Cantor, Mueller & Player

[57] ABSTRACT

A method for the separation of long-chain nucleic acids from other substances in solutions containing nucleic acids and other materials, comprising fixing long-chain nucleic acids in a nucleic acid-containing solution onto a porous matrix, washing the porous matrix to separate the other substances from the long-chain nucleic acids, and removing the fixed long-chain nucleic acids from the porous matrix is disclosed. A device for carrying out the method of the claimed invention is also described.

21 Claims, 3 Drawing Sheets

METHOD FOR SEPARATING LONG-CHAIN NUCLEIC ACIDS

The present invention relates to the separation of long-chain nucleic acids from other substances in solutions containing nucleic acids and other materials, and more particularly nucleic acid/protein mixtures from biotechnical preparations from bacteria, viruses, animal and vegetable tissues and cells, more particularly cell ingredients and/or degradation products thereof as well as components of body liquids which components are not long-chain nucleic acids, and to the device for carrying out the method.

The preparation of nucleic acid from natural sources, and more particularly from viruses, bacterial and eucaryotic cells, cell aggregates or tissues as well as body liquids is a key technique for various preparative and analytical problem solutions in biology and medicine. Some important applications may be mentioned by way of example hereinafter:

Molecular biology uses vehicles capable of replicating DNA fragments, which include plasmids, phages, viruses, etc. In order to be able to use the DNA- or RNA-processing enzymes, first a highly purified DNA or RNA is needed. The same is applicable to genetic analyses of, for example, viruses or genomic DNA from tissue. For specific detection of certain characteristics of nucleic acids such as, for example, restriction polymorphisms, said nucleic acids prior to analysis are subjected to an enzymatic degradation, and thus they must be present in such a purity that these methods are usable. The methods so far known do not allow one to extract and to concentrate the DNA/RNA by following similar and simple instructions, because starting materials may be so different (i.e., solutions containing nucleic acids and other materials, more particularly nucleic acid/protein mixtures from a biotechnological preparation, tissue, blood, sputum, cell cultures, bacteria, fungi, renal and fecal excrements).

The problems will become more clearly evident in consideration of virus diagnostics, for example the detection of Hepatitis B-DNA in blood and liver biopsies, the individual assignment in criminology, forensic medicine or paternity analysis. The analytical methods to be employed require cellular nucleic acids from very different sources, such as sperm or tissue (fresh, carbonized, frozen, dried etc.), for use in technically comparable kinds of subsequent analysis The methods as so far known for the purification of longchain nucleic acids require centrifugation steps of extended duration or aqueous phenol/two-phase extractions. Such procedures are rather intensive in personnel and equipment cost and, moreover, too expensive to be simply realizable in an automated operation. Furthermore, the known and conventionally used purification methods involve the use of expensive equipment such as cooled centrifuges and ultracentrifuges which, in addition, consume valuable materials such as cesium chloride for density gradient centrifugation and rotor insertions for one-time use.

A method described in EP-A- 0 104 210 and based on the use of HPLC devices is suitable for a chromatographic separation of nucleic acids; however, long-chain nucleic acids such as, for example, λ-phage DNA are damaged by the mechanical action.

From Bernardi, G. (1971), "Methods in Enzymology" (Grossman, L. & Moldave, K., Edit.) Vol. pages 95 to 139, Academic Press, N.Y., is known a method for the separation of nucleic acids from proteins, lower molecular weight substances and cellular components such as oligo- and polysaccharides by chromatographic purification on hydroxylapatite (HAP). This method has also been used for the purification of plasmid and λ-phage DNA (cf. Colman, A. et al., 1978, Eur. J. Biochem. 91, 303 to 310; Shoyab, M. & Sen, A., 1978, J. Biol. Chem. 253, 6654 to 6656; and Johnson, T. R. & Ilan, J., 1983, Anal. Biochem. 132, 20 to 25). However, this method is not comparable to the method according to the present invention. Thus, for example, the separation efficiency, expressed in milligrams of nucleic acid per grams of separating gel, which amounts to about 1 mg/1 g in the method according to the present invention, is about 100 times higher than that of the HAP method. For long-chain nucleic acids the separation on HAP results in high losses in yield, especially with cellular DNA, and requires high phosphate and urea concentrations in the eluting buffer, which adversely affects further processing of the separated long-chain DNA. The known gel permeation procedures are not capable of separating high molecular weight nucleic acids from other high molecular weight substances such as proteins and polysaccharides, since these gel materials will only select by size and shape.

For the direct hybridization reaction the product purity as obtained by known methods is usually sufficient. However, for a number of detection procedures the concentration of the purified long-chain nucleic acid is too low for allowing direct detection by hybridization.

As examples there may be mentioned the analysis of AIDS virus nucleic acids in much underrepresented infected cells of a lymph node biopsy or the detection of a restriction fragment length polymorphism (RFLP) in a small amount of cells obtained upon an amniocentesis or chorion biopsy.

If specific nucleic acid sequences are to be enzymatically amplified, then the nucleic acid to be amplified must be present in such a purity that enzymes such as polymerases will not be inhibited (Saiki, R. K. et al., 1985, Science 230, 1350 to 1354). An essential purification step of the known methods is the use of a phenolic extraction in order to efficiently effect the removal of proteins and organic agents which may inhibit enzymes. However, phenol is a strong poison to skin and liver and should be processed only by well trained staff under strict precautions. Moreover, liquid extractions are time-consuming and intensive in personnel.

So far such purifications of long-chain nucleic acids, more particularly in molecular biology, could be carried out only in research institutes, for the known methods are time-consuming and intensive in instrumentation and cost. Moreover, due to the chemicals used the methods are dangerous to health. A typical instruction for operation may be classified into the following steps:

a) the disintegration and digestion of the cells or tissues or body liquids for which a number of methods may be employed, such as mechanical methods (for example milling) in combination with other physical methods (for example a boiling procedure "Koch-Verfahren"), with enzymatic methods (using, for example, proteinase K. lysozyme etc.,) and with chemical methods (using, for example, sodium hydroxide solution, diethyl pyrocarbonate), and which renders the cell contents accessible to further enzymes and reagents;

b) a coarse clarification of the solution from cell debris by means of a centrifuge;

c) steps for the removal of proteins and first accumulation of the nucleic acid, usually by utilization of a two-phase system consisting of phenolic phase/aqueous phase; and d) high purification techniques such as ultracentrifugation.

The known methods for purifying long-chain nucleic acids (>20 kB-molecular weight >13 million Dalton) have in common that they are difficult to rationalize if the nucleic acid preparations are to be carried out as routine operations. Such condition, for example, exists in laboratories of molecular biology which permanently have to provide highly pure plasmids or phage DNA.

In medical diagnostics there is an urgent demand to obtain new information and knowledge from the analysis of genetic material. For instance, for diagnosis of hepatitis only the direct detection of the virus will provide information on the infection, and for the detection of a genetically caused protein deficiency, for example of a thalassemia, genetic analysis is required. The work-up of the material to be analyzed (DNA or RNA), more particularly with large sample numbers, has proven to be a crucial barrier on the route to genetics-based diagnostics, if the latter is to match the known serologic methods with respect to the applicability thereof to large sample populations.

The importance of an automated nucleic acid work-up is extreme. This mode of operation is a prerequisite for generally applicable genetics-based diagnostics, which, with respect to the importance thereof, would correspond to the widely used methods of serologic diagnostics. Both methods cover areas such that respective information obtainable from each will add to each other in a complementary manner.

While in immunology the cell or virus products may be qualitatively and quantitatively determined, by genomic analysis a diagnosis is verified on the basis of the information stored in the nucleic acid.

Gene technology enables an extremely high-resolving diagnostic test to be effected, due to the fact that nearly each individual structural element of the genetic store, comprising up to billions of structural elements, can be examined. This procedure allows one to determine the presence or absence of infectious genetic material, for example of an AIDS causative agent, or to recognize genetic diseases, such as muscular dystrophy, without gene products having to be expressed (for example, protein/antigens) or without a determination of the absence thereof.

Furthermore, biotechnology, and more specifically gene technology, enables products to be produced by means of transformed microorganisms. However, there arises the very serious problem that upon use of products prepared by biotechnology one cannot exclude the possibility that potentially noxious genetic information is transferred into the cell or into the genetic information of the recipient. Such transfer may cause transformation, infection, resistance to antibiotics etc. to occur.

The problem becomes more serious with the use of increasingly homologous transformed cell systems, such as hamster ovary cells, human fibroblasts, cancer cells, etc., rather than systems using *E. coli* or yeast. This change in cell systems is pursuant to the goal of producing human-identical protein products, which with respect to conformation and, above all, modification (such as glycosylation and other post-translational modifications) are equivalent to human proteins.

However, simultaneously therewith is the enhanced danger of a possible transformation of human cells of a patient by homologous DNA sequences or adapted vector systems. Such transformation may carry over properties such as self-reproducibility, resistance behavior, the presence of strong promotors, enhancer elements, and oncogenetic information, such as "gene dose" effects. Such apprehensions were also present with respect to genetic information obtained from *E. coli,* yeast, and *B. subtilis,* etc. Thus, the danger exists that preparations contain nucleic acid which either directly acts as a pathogen, such as in the case of certain viruses and of oncogenetic DNA, or which may indirectly act to initiate a cancer by becoming integrated in the recipient's DNA and initiating mutations thereupon. This is why it is desirable that all therapeutic products are as free from nucleic acids as possible. Thus, at present the American health authorities {Food and Drug Administration (FDA)} recommend that a dose of not more than 1 to 10 pg/day of DNA may be administered.

Upon application of the methods of the prior art, depending on the kind of production system used, in the first steps of purification of the biotechnicall prepared products varying amounts of nucleic acid are obtained. Only traces of contaminating nucleic acid are present once the cells continuously secrete the synthesized product, so only undesiredly lysed cells will significantly release nucleic acids. However, the total cell equivalent of nucleic acids may also be present as contamination, if after batch production the host cells are completely lysed for intended product release or for killing. In this latter case, the first step frequently is the precipitation of the DNA/RNA by polycations, such as polyimine. However, this step does not lead to a complete removal of the substances.

Therefore, it is the object of the present invention to provide a process for removing long-chain nucleic acids from tissues and body liquids which:

a) in a similar manner allows the nucleic acids to be extracted and concentrated from various starting materials, such as tissue, blood, sputum, cell cultures, bacteria, fungi, renal and fecal excrements, as well as from vegetable tissue from callus cultures, roots, etc.;

b) requires no long-time centrifugation steps, and more specifically no ultracentrifugation;

c) can be carried out without expensive equipment, and more specifically without refrigerated centrifuges and ultracentrifuges, and without using valuable material, such as cesium chloride for density gradients or rotor insertions for one-time use;

d) ensures high purity of the nucleic acid to be attained;

e) works without a phenolic extraction step; and f) is suitable for being automated;

and by means of extraction of the long-chain nucleic acid, separates mixtures of long-chain nucleic acids and other materials, such as those obtained when products are biotechnologically produced.

In the EP-A- 0 104 210 there has been described a method for separating nucleic acids up to plasmid size (<10,000 base pairs $\triangleq$6 million Dalton). By using the material described therein, which is distinguished by a highly porous silica gel provided with an anion exchanger coating as employed in HPLC chromatography that is used as a carrier, for example, prepurified plasmids may be prepared in a highly pure state. Nevertheless, centrifugation steps and precipitation steps are necessary, which are not suitable for application in bulk analysis and preparation, respectively. One crucial drawback with larger molecules, for example λ-phage DNA, is that during the chromatographic separation of particles <10 μm the shear forces become so high that intact molecules cannot be recovered. This is all the more applicable to cellular DNA, which has a length many times that of λ-phage DNA.

The object of the present invention is attained by a method wherein the long-chain nucleic acids from bacterial cells, viruses, vegetable and animal tissue cells, and/or cells from body liquids after disintegration under mild conditions or from mixtures containing nucleic acids and other materials, more specifically nucleic acid/protein mixtures from a biotechnical preparation, are fixed on a porous matrix, the substances to be separated therefrom are washed out from the matrix, and the fixed nucleic acids are subsequently removed from the matrix.

The porous matrix preferably consists of a material for chromatography, such as silica gel, diatomite, aluminum oxide, titanium dioxide, hydroxylapatite, dextran, agarose, acrylamide, polystyrene, polyvinyl alcohol or other organic polymers, derivatives or copolymers of the above-mentioned carrier materials, the surfaces of which preferably have been modified, more specifically with chemical groups exhibiting anion exchanger activities.

In a particularly preferred embodiment, the porous matrix consists of modified silica gel particles having a particle size of from about 15 to about 250 μm, and preferably from about 25 to about 40 μm. The pores have diameters of from about 50 to about 2,500 nm, preferably from about 100 to about 2,500 nm, with about 400 nm particulary preferred. The modification of the silica gel is preferably effected by reacting the carrier material with a silanating reagent to form an anion exchanger.

As disclosed in EP-A- 0 104 210, this reaction employs gamma-glycidyloxypropyl trimethoxysilane and N,N-dimethylaminoethanol as reactants.

The process according to the invention, inter alia, makes it possible to avoid a phenolic extraction of the digestion mixture for purifying the long-chain nucleic acids from interfering components.

In the process according to the invention, it is recommended to use hydrophilic surfaces, since nucleic acids, and more particularly long-chain nucleic acids, tend to strongly interact with the matrix if salt solutions of high ionic strength are used. The strong hydrophobic interactions may give rise to contamination and yield problems The mild enzymatic proteolysis may be carried out either alone or in combination with the application of mechanical means. A number of methods are available, namely mechanical methods (for example, milling) in combination with other physical methods (for example, a boiling procedure "Koch-Verfahren"), enzymatic methods (using, for example, proteinase K, lysozyme, etc.), and chemical methods (using, for example, sodium hydroxide solution or diethyl pyrocarbonate).

These methods may be employed either alone or in combination with the method according to the invention for the extraction of long-chain nucleic acids. Some of these known methods (T. Maniatis, E. F. Fritsch, J. Sambrook (CSH), 1982, "Molecular Cloning" (C.S.H.)) utilize sodium dodecylsulfate (SDS) or Sarcosyl(®) as detergent or a solubilizing and protein-denaturing agent. In the presence of more than 0.1% SDS (preferred concentrations are from 0.1 to 2%), the bond of DNA/RNA to the polycationic surface of the carrier is affected and greatly reduced. If the use of SDS is inevitable for the digestion, then the aqueous phase must be admixed with phenol and/or chloroform, i.e., a liquid-liquid extraction is necessary in order to remove the SDS. An alternative is solid phase extraction by means of hydrophobically-coated carriers (reverse-phase carriers) prior to employing the method of the present invention.

In the method according to the invention, the substances to be separated from the long-chain nucleic acids are removed by thoroughly washing them out with a washing solution of low ionic strength. The eluate formed is virtually free of long-chain nucleic acids. This is particularly advantageous in the removal of long-chain nucleic acids from products having been biotechnologically produced. The method according to the invention allows the separation of more than 99% and up to 100% of long-chain nucleic acids from nucleic acid/protein mixtures.

The porous matrix employed in practicing the method according to the present invention specifically complies with the following criteria, which makes it particularly useful for removing long-chain nucleic acids from nucleic acid/protein mixtures:

1. High affinity for long-chain nucleic acids;
2. low affinity for other materials, and more particularly for proteins;
3. no nonspecific interactions with other materials, such as proteins;
4. no nonspecific retention of other materials, more specifically of proteins due to inclusions that are physically caused (narrow pores);
5. sterilizability;
6. low bleed-off of the porous matrix;
7. no toxic decomposition products of the porous matrix;
8. high capacity of the porous matrix for nucleic acids;
9. regenerability;
10. physiological elution conditions; and
11. high process flow velocity.

The separation of the long-chain nucleic acids from the matrix is effected by rinsing the porous matrix with a solution of high ionic strength (high salt concentration).

In the purification of plasmid-DNA, for example from recombinant *E. coli*, various methods may be employed for the disintegration of the host cells. By these methods, centrifugation at about 12,000 g produces the so-called clear lysate, a clear supernatant having been mostly rid of cell debris and chromosomal DNA, which supernatant contains plasmid-DNA, RNA, proteins and other soluble components. Here may be mentioned the lysozyme/Triton method or SDS method, (cf. Maniatis et al.), the NaOH/SDS method (Birnboim, H. C. & Doly, I., 1979, Nucl. Acids Res. 7, 1513 to 1523; Ish-Horowicz, D. & Burke, J. F., 1981, Nucl. Acids Res. 2989 to 2998), the phenol method (Klein, R. D. et al., 1980, Plasmid 88 to 91) and the "Boiling" method (Holmes, D. S. & Quigley, M., 1981, Anal. Biochem. 114, 193 to 197).

The clear lysates, if they do not contain significant amounts ($\leq 0.01\%$) of ionic detergents such as SDS, may be directly purified by means of the method of the present invention. With selection of suitable conditions of ionic strength (preferably from 0.5 to 0.7 M), for example, proteins, lipids, RNA and smaller molecules are separated via adsorption to the porous matrix of long-chain DNA, more specifically DNA from plasmids, the latter materials being bound to the carrier material. The addition of urea to the loading buffer does not affect the binding behavior of the long-chain DNA, while it optimizes the separation efficiency with respect to proteins. Thereby the high capacity of this material (about 1 μg of nucleic acid per 1 mg of the porous matrix) is specifically exploited for DNA, in spite of the high molar excess of cellular RNA.

Nonspecifically bound RNA and proteins are removed from the porous matrix in a few washing steps, by washing with buffer solutions of low ionic strength. Then the elution is carried out by extracting the matrix with buffers of high ionic strength.

Due to the unusually high separation efficiency of the claimed method, between RNA/protein on the one hand, and long-chain DNA on the other hand, subsequent RNase and possibly proteinase treatment(s), as usually employed, are not required. If the clear lysate is SDS-free, such as after a potassium acetate precipitation or as produced by a lysozyme/Triton X-200(®) lysis, after adjustment of the ionic strength from 0.5 to 0.7 M, the lysate may be directly passed through the porous matrix in order to extract long-chain plasmids. Otherwise, SDS and proteins may first be extracted by phenolization and admixing with chloroform, followed by DNA extraction by means of the process according to the invention. Phenol dissolved in the lysate does not interfere with the plasmid-binding property of the porous matrix.

If the volume of the lysate is very large, it is recommended first to precipitate DNA with polyethylene glycol (PEG), ethanol or isopropanol. Then the pellet is dissolved in tris-buffer, the solution is adjusted to the desired ionic strength and passed through the porous matrix. Thereby DNA is extracted from the solution, washed with buffers having lower ionic strengths in subsequent washing operations, and thereafter reextracted with tris-buffer of high ionic strength. Then, if desired, DNA may be desalted by a) dialysis, b) precipitation or c) gel permeation chromatography.

The plasmid-DNA isolated by means of the method according to the invention exhibits properties which are at least as good as those of the DNA isolated using known purification methods. The plasmid DNA may be processed with restriction enzymes and DNA ligases; it is further capable of being sequenced or transfected.

λ-Phages are vehicles frequently used for the transportation of recombinant nucleic acids, and are preferred over plasmid vectors for many applications, as they a) after protein encapsulation (in vitro packaging) very efficiently introduce alien DNA into cells and, thus, are suitable for establishing comprehensive gene banks;

b) may take in small as well as very large DNA fragments;

c) have good storability;

d) and are easy to cultivate.

Many cloning experiments start with establishing a λ-gene bank, and more specifically a randomly established gene bank. As at this stage only an insufficiently characterized DNA is employed, warranting biological safety is often a problem. Thus, for example, in cloning oncogenetic substances or viral sequences (i.e., HTLV-III/LAV-1) safety strains and safety phages of the biological safety level 2 (B2) have to be employed and processed under high laboratory safety conditions (L2 or L3; ZKBS, Berlin; cf. 5th revised version of handling newly recombined DNA). In the course thereof, work-up steps such as centrifugations, and more particularly elaborate, time-consuming and expensive cesium chloride-gradient centrifugations, and harvesting of the phages constitute safety problems for laboratory and staff.

The method according to the invention renders it possible to purify phages/phage-DNA by evading centrifugation steps. A grown or lysed bacterial culture may be completely worked up, if desired, in a sterile bank to yield λ-DNA having a purity conforming to that of cesium chloride-purified preparations.

Also, a single-stranded DNA, for example M13 phage-DNA, can be purified by using the method of the present invention. From cell lysates single-stranded DNA in high yield and purity may be used for sequencing and hybridization experiments. After the phages have been isolated, the single-stranded DNA is released and adsorbed onto the porous matrix. The interfering components are removed by washing.

For isolation of cellular DNA from tissues of various origin the material is disintegrated and digested using known methods. Thus, a mechanical homogenization, for example under nitrogen, in a ball mill or by efficient maceration and shearing of the material is followed by proteolytic digestion in the presence of denaturing and/or solubilizing agents. Proteinase K is a preferred enzyme for the proteolytic digestion, as it efficiently leads to a lysis of cells and cell nuclei, even in the presence of 1% of SDS and EDTA. According to prior art, SDS and the proteins have to be removed by time-consuming liquid-liquid extractions, which steps are followed by a dialysis and precipitation of DNA. This procedure is elaborate and difficult to automate. However, the method according to the invention allows one to bring long-chain DNA from the sample materials as mentioned above into solution under mild conditions, to fix the DNA on the porous matrix while evading any steps of phenol extraction, and subsequently to elute the DNA under mild conditions in a small volume (i.e., 0.5 to 5 ml, and preferably 1 to 3 ml).

Infections with viruses play an important role in transfusion and transplantation medicine, and generally with immunosuppressed patients. For example, an acute CMV (cytomegalovirus) infection can be detected by an analysis of renal excrements. According to the state of the prior art, the bacteria are separated from urine by a filtration step or low-speed centrifugation step, and thereafter the virus-DNA is released from the protein sheath and purified by concentration as simultaneously occurring. To this end ultracentrifuges were used in prior art.

The method according to the invention utilizes the described porous matrix by lysing the CMV viruses in situ by addition of urea, detergent and buffer, whereupon the DNA (130 to $150 \times 10^6$ Dalton) is released. The DNA is then concentrated by adsorption onto the porous matrix and washed with buffer solutions having low ionic strength. Thereafter the DNA is eluted using a buffer of high ionic strength. If further analysis is followed by a dot-blot technique, it is not required to desalt the DNA.

The use of a porous matrix consisting of a chromatography material on the base of silica gel, diatomite, aluminum oxide, titanium dioxide, hydroxylapatite, dextran, agarose, acrylamide, polystyrene, polyvinyl alcohol or other organic polymers, derivatives of or copolymers of the above-mentioned carrier materials, the surfaces of which preferably have been modified so that the matrix exhibits anion exchanger activities, warrants the advantages of the method according to the invention. The particle size of the porous matrix based on silica gel is, for example, about 15 to about 250 $\mu$m, and preferably about 25 to about 40 $\mu$m, and the pore diameter is about 50 to about 2,500 nm, preferably about 100 to about 2,500 nm, and particularly preferred about 400 nm.

The device for carrying out the method according to the invention consists of a container made of a material which is resistant to the operation conditions in accordance with the method of the invention. The container receives the porous matrix and has at least one inlet and outlet openings each.

FIG. 1 shows schematically a container, according to a preferred embodiment, for the porous matrix consisting of a cartridge 1, which preferably forms a substantially cylindrical hollow body and the side walls 2 of which consist of a material which is resistant to the working conditions (presence of more or less aggressive chemicals and corrosive salts). The side walls 2 preferably are made of a plastics material Particularly simple is the preparation of the cartridges by using a shrink tube, for example one made of polytetrafluoroethylene (PTFE).

The inlet opening 3 and outlet opening 4 are delimited by filters 5 a and 5 b. In a preferred embodiment the filter consists of a hydrophilic material, such as glass, hydrophilic plastics or plastics material coated with a hydrophilic material. However, hydrophobic materials may also be employed. The inlet opening 3 may optionally be shaped so that a Luer Lock system 6 is directly connectable to the inlet cannula. The outlet opening 4, in a preferred embodiment, has an internal tube 8, preferably made of silicone, which is connected to the filter 5 b and preferably does not exceed the end of the outlet cannula 9. The eluate from the cartridge is discharged by a tube 10 which preferably is made of a plastics material, and particularly of a hydrophilic plastics material. Nevertheless, hydrophobic plastics materials such as PTFE may be used as well. The container may also be manufactured by injection molding.

Figure 3:
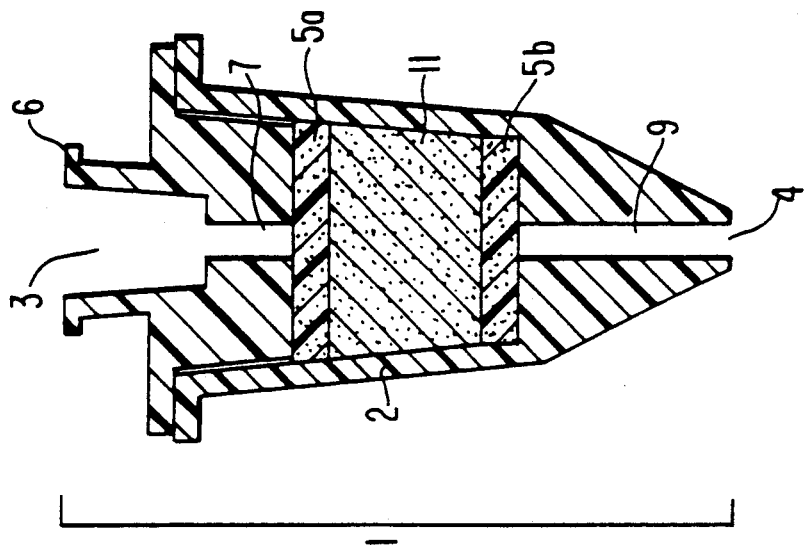
Figure 2:
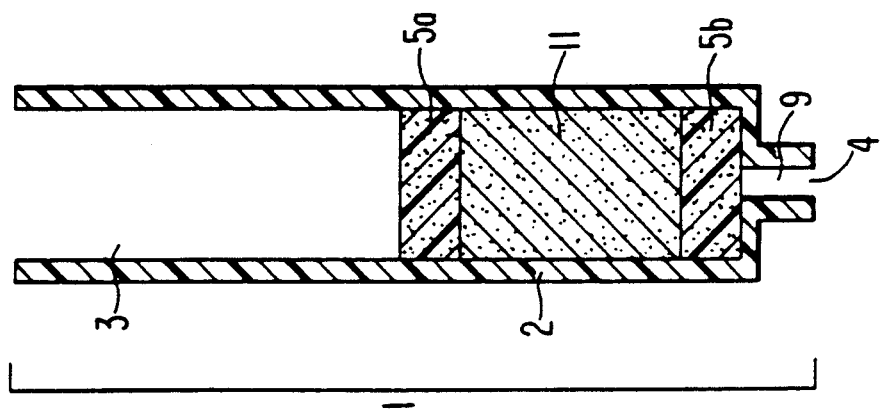

FIG. 2 shows schematically another preferred embodiment of a container according to the invention, which can preferably be produced by means of injection molding. The reference numbers correspond to the following:

1 cartridge
2 wall
3 inlet
4 outlet
5a porous fritt
5b porous fritt
9 outlet tube
11 porous resin FIG. 3 shows still another preferred embodiment of a container according to the invention. Also, this container can be produced by injection molding. The reference numbers correspond to the following:

1 cartridge
2 wall
3 inlet
4 outlet
5a a porous fritt
5b porous fritt
6 luer-lock connector
7 inlet tube
9 outlet tube
11 porous resin The internal volume of the container for the porous matrix 11 depends on the intended use. Usually for analytical procedures the internal volume is about 0.02 to 5 cm$^3$, and preferably 0.1 to 1 cm$^3$. If solutions containing nucleic acids and other materials are to be purified on a preparative scale, containers having larger dimensions may be used as well. The porous matrix 11 preferably consists of a silica gel-based anion exchanger. The pore diameter of the material is about 50 to about 2,500 nm, preferably about 100 to about 2,500 nm, and particularly preferred about 400 nm, at a particle size of from about 15 to about 250 $\mu$m, and preferably about 25 to about 40 $\mu$m.

A mixture of disintegrated cells from tissue or body liquids, after proteolysis under mild conditions optionally in combination with the application of mechanical means, is introduced into the cartridge via the inlet opening and comes into intimate contact with the porous matrix. Thereupon the matrix extracts the long-chain nucleic acids from the mixture, whereas the other substances will leave the cartridge via the outlet opening. Attention is to be paid that the applied mixture of the digested material has a low ionic strength. For example, at an ionic strength of about 300 mM of NaCl long-chain RNA and DNA are adsorbed, whereas proteins and lower molecular weight substances are not adsorbed to a significant extent; at concentrations higher than 500 mM of NaCl only long-chain single-stranded DNA and a double-stranded DNA are bound, while at salt concentrations around 700 mM NaCl only long-chain double-stranded DNA will be adsorbed on the porous matrix.

Figure 4:
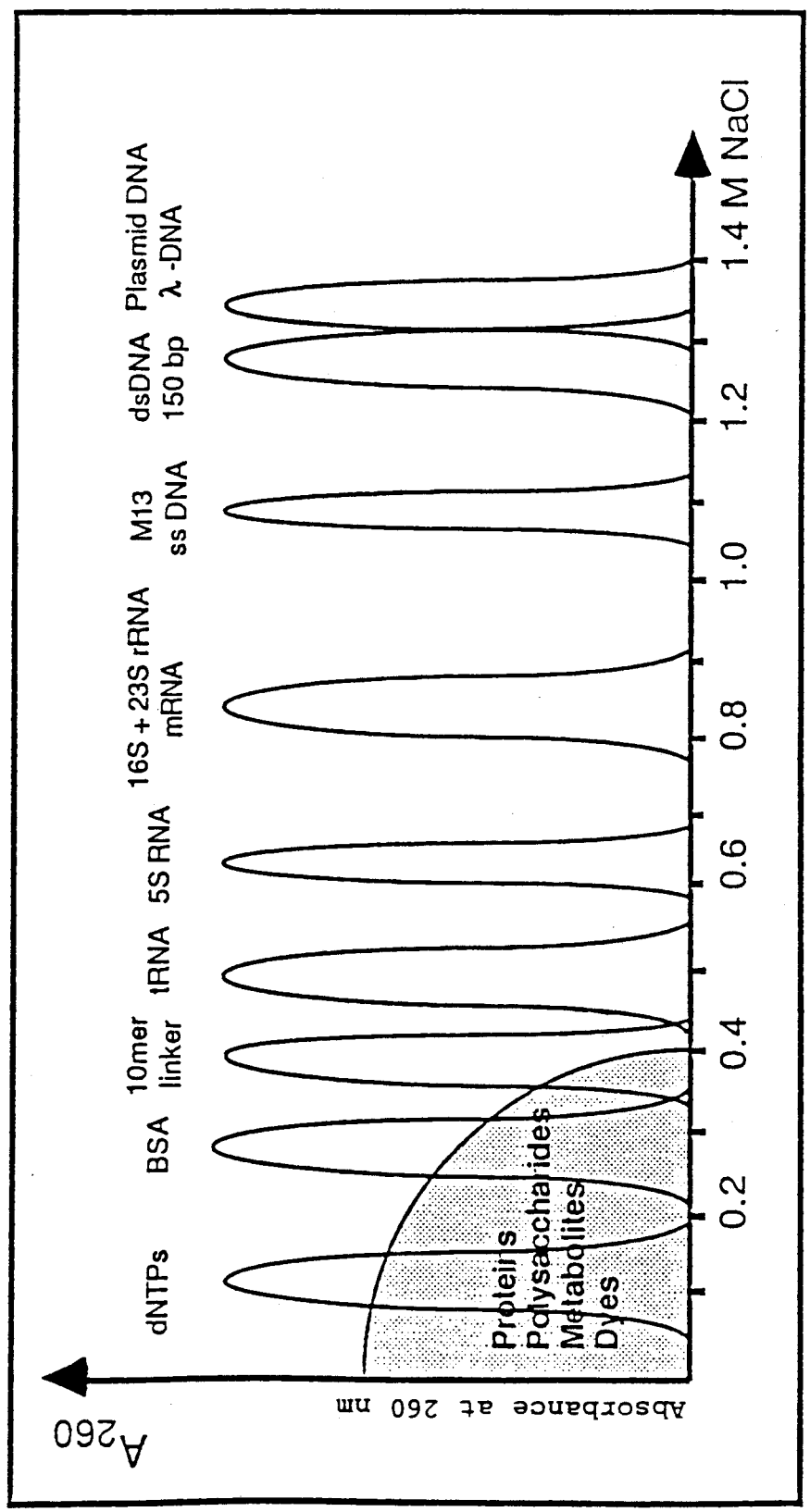

FIG. 4 demonstrates the typical elution profiles with NaCl-gradient elution at pH 7.0. The absorbance of different substances at 260 nm is plotted versus NaCl concentration. This exemplary diagram shows the very good separation of the biomolecules. The dotted area symbolizes the range in which proteins, polysaccharides, low molecular weight metabolites and dyes are eluting off the matrix. This happens in the range of from 0 to 0.4 M NaCl. At 0.1 M, for example, are eluted nucleotides, whereas the standard protein BSA (bovine serum albumin) elutes at 0.3 M NaCl concentration. The decamer linker, however, elutes at about 0.4 M NaCl. From the graph it can be seen that tRNA elutes at 0.5 M, 5 S RNA at 0.65 M, 16 S and 23 S rRNA and mRNA between 0.8 M and 0.9 M, M13-phage and other single-stranded (ss) DNA at 1.1 M, double-stranded (ds) DNA of 150 basepairs at slightly below 1.2 M and finally plasmid DNA, for example $\lambda$-phage DNA, at 1.3 M NaCl, respectively, the latter one slightly overlapping with the former one. The values are determined only approximately because they might vary depending on the experimental conditions, as one skilled in the art would expect.

If the porous matrix is synthesized under conditions which do not result in a maximum surface charge density, then the separation profile is altogether shifted to lower ionic strengths, whereas the separation efficiency is not significantly affected. This latter effect is even desired if the DNA must be eluted at a lower salt concentration.

After the sample has left the cartridge, the cartridge is carefully rinsed with a washing solution of the desired ionic strength (as set forth above), whereupon the long-chain nucleic acids are desorbed from the porous matrix. This is effected by eluting with a solution of high ionic strength. To this end, in the simplest case the second solution may be introduced through the same inlet opening 3 and be drained through the same outlet opening 4. However, there may also be used cartridges, if desired, which comprise different inlet openings and different outlet openings, respectively, for the solutions having low ionic strength and high ionic strength.

In a further embodiment the method according to the invention may be realized in practice as a "batch" procedure, which is distinguished by particularly simple handling. The batch procedure has the advantage of preventing shearing forces to high molecular weight nucleic acids. With this procedure, nucleic acids up to 500,000 basepairs (molecular weight of approximately 300 million Dalton) can be isolated on a preparative scale without degradation of sensitive molecules by a shearing force. A porous matrix suitable for extracting long-chain nucleic acids is charged in a reaction vessel in a sufficient amount and intimately mixed with the sample to be extracted, with the ionic strength of the solution being adjusted as indicated above. The long-chain nucleic acids are adsorbed onto the porous matrix. The contaminating components are removed by several washing steps. Thereafter the long-chain nucleic acids are separated under mild conditions from the matrix by elution using a buffer having the desired ionic strength. The porous matrix preferably consists of an anionic exchanger based on a surface-modified chromatography material from silica gel, diatomite, aluminum oxide, titanium dioxide, hydroxylapatite, dextran, agarose, acrylamide, polystyrene, polyvinyl alcohol or other organic polymers, derivatives of or copolymers of the above-mentioned carrier materials. Based on modified silica gel the pore diameter is about 50 to about 2,500 nm, preferably about 100 to about 2,500 nm, and particularly preferred about 400 nm, and the particle size is about 15 to about 250 $\mu$m, and preferably about 25 to about 40 $\mu$m.

The invention is further illustrated by means of the following examples:

EXAMPLE 1

The preparation of a plasmid (2860 base pairs) is carried out as follows:

Subsequent to an alkali/SDS digestion procedure, a 100 ml culture of plasmid-transformed HB-101 *E. coli* cells is centrifuged in LB-ampicillin medium (see Maniatis et al.) at 5000 g and 5° C. for 10 minutes. The supernatant is carefully decanted, and the cell pellet is resuspended in 2 ml of 50 mM glucose, 25 mM of Tris-HCl, pH 8.0, 10 mM of EDTA.

The sample is allowed to sit at 20° C. for 5 minutes. Then 4 ml of a freshly prepared 1% SDS-solution in 0.2 M NaOH are added thereto and carefully admixed, and the mixture is incubated on ice for 5 minutes. Thereafter, 3 ml of a cold sodium acetate solution (3M Na-acetate, 2M acetic acid) are added thereto and carefully admixed, and the mixture is incubated on ice for another hour. After 10 minutes of centrifugation at about 10,000 g at 10° C., a clear plasmid-containing supernatant is obtained. If potassium acetate is used instead of sodium acetate, most of the SDS is precipitated.

In the case of large lysate volumes, it is recommended first to precipitate the DNA with PEG, ethanol or isopropanol. Then the pellet is dissolved in 10 mM of Tris-buffer, pH 7.5, 1 mM of EDTA, adjusted to 0.6 M of NaCl and passed over 200 mg of the separating gel. Thereby the DNA (about 100 82 g) is extracted from the solution. In the subsequent washing step the gel phase is washed with 0.8 NaCl, 50 mM of Tris-HCl buffer, pH 7.5, 1 mM EDTA and extracted with about 1 ml of 1.2 M NaCl, 50 mM Tris-HCl buffer, pH 7.5, 1 mM EDTA. Thereafter the DNA may be desalted by dialysis, precipitation or gel permeation chromatography.

EXAMPLE 2

The preparation of $\lambda$-phage DNA is carried out as follows:

A grown and lysed $\lambda$-phage/*E. coli* culture (50 ml) is centrifuged at 5000 g and room temperature for 15 minutes or allowed to sit on ice for 30 minutes (cf. Maniatis, T. et al.). The supernatants or parts thereof are filtered through narrowpore sterile filters, for example 0.45 $\mu$m, to retain intact cells or floating cell debris.

The suspension of phages is efficiently rid of cellular DNA by passing it through a cartridge (FIG. 1) at an ionic strength of from 0.5 to 0.7 M NaCl. The bed volume of the porous matrix is to be selected so that the capacity is sufficient for the cellular DNA released from the lysed cells (about 200 mg of porous matrix per 100 ml of lysate).

The filtrate is treated with EDTA (200 mM). Upon simultaneous addition of 4 M of urea, the DNA of the phages is released and, by means of another filtration through the cartridge, specifically adsorbed on the anion exchanger. Then the cartridge is washed with 0.8 M NaCl, 50 mM Tris-HCl buffer, pH 7.5, 1 mM EDTA, and the DNA is eluted with about 1 ml of 1.2 M NaCl, 50 mM Tris-HCl buffer, pH 7.5, 1 mM EDTA.

The phage DNA thus obtained may be precipitated with PEG or isopropanol. It is also possible to desalt the phage DNA by means of dialysis (cf. Maniatis, T. et al.). A DNA preparation having high purity is obtained.

EXAMPLE 3

The preparation of M-13 phage DNA is carried out as follows (an analogous procedure is used for the preparation of single-stranded DNA):

The phage lysate is obtained in a conventional manner (cf. EXAMPLE 2) by disintegration of the cells. After the removal of the cell debris (for example by centrifugation at 5000 rpm for a period of 5 minutes), RNase A is added to a final concentration of 10 $\mu$g/ml, and an incubation is allowed to occur at 37° C. for 30 minutes. If the volume of the lysate is too large, a PEG (polyethylene glycol) precipitation of the phage is recommended. 0.3 volumes of 30% PEG and 1.5 M sodium chloride are added and well admixed, and the mixture is allowed to sit on ice for 30 minutes. The precipitated bacteriophage particles are separated from the solution by centrifugation at 10,000 g for 15 minutes. The supernatant is carefully aspirated, and the phage pellet is dissolved in 20 $\mu$l of 10 mM Tris, 1 mM EDTA, pH 7.5. Another part by volume of extraction buffer (2% Triton X-100(®), 7 M urea, 100 mM EDTA, pH 7.5) is added, and the mixture is heated at 50° C. for 15 minutes to release the single-stranded DNA.

The cartridge is equilibrated with a buffer of low ionic strength comprising 400 mM sodium chloride, 50 mM MOPS (3-N-morpholino-propanesulfonic acid), 15% ethanol and 1 mM EDTA at pH 7.0. The sample is passed through the cartridge. Then the cartridge is carefully washed with a buffer having a sodium chloride concentration of 750 mM and otherwise a composition as mentioned above. The single-stranded M-13 DNA may be eluted using an elution buffer having a composition of 1.1 M NaCl, 50 mM MOPS, 15% ethanol and 1 mM EDTA at pH 7.0.

EXAMPLE 4

The isolation of cellular DNA from sperm is carried out as follows:

One hundred $\mu$l of sperm are suspended in 1 ml of 500 mM NaCl, 10 mM EDTA, 40 mM DTE, 10 mM Tris-HCl buffer, pH 7.5, 1% Triton, 4 M urea and 20 $\mu$g/ml of proteinase K and incubated at 37° C. for 2 hours. After centrifugation at about 5000 g for 5 minutes, the supernatant is passed through the separating gel in a cartridge. The flow velocity of the supernatant through the cartridge is about 1 ml/min.

Alternatively the "batch" process may be used. In said process the supernatant is intimately mixed with the separating gel by rotation in a 1.5 ml Eppendorf reaction vessel for 15 to 30 minutes. The next step comprises washing the gel five times in the batch process or washing the gel in cartridge with 5 ml of washing buffer (800 mM NaCl, 50 mM Tris-HCl buffer, pH 7.5, 1 mM EDTA), followed by elution with about 1 ml of 1.2 M NaCl, 50 mM Tris-HCl buffer, pH 7.5, 1 mM EDTA. The elution yield is higher than 80%. The DNA may further be desalted by dialysis or precipitation (cf. EXAMPLE 1). The DNA may be cut with restriction enzymes and is suitable for analysis with the Southern-Blot method (cf. T. Maniatis et al.).

EXAMPLE 5

The preparation of genomic DNA from liver biopsy material is carried out as follows:

Liver biopsy material is mechanically homogenized according to the Potter procedure or any comparable method. To the homogenate proteinase K lysis buffer (cf. EXAMPLE 3), 10-fold volume, is added and the mixture is incubated at 37° C. for 2 hours. The following work-up steps are as described in EXAMPLE 4.

EXAMPLE 6

The preparation of papilloma-virus DNA from verruca biopsy tissue is carried out as follows:

After a mechanical disintegration (liquid nitrogen, ball mill, mechanical squeezing) of verruca biopsy material, in the same manner as described in EXAMPLE 5, ten times the amount of lysis buffer is added, the mixture is incubated at 37° C. for 6 hours, and the DNA is worked up as described in EXAMPLE 4. The procedure provides a high molecular weight DNA, which is a mixture of cellular DNA of the human cells and papilloma-virus DNA from the proteolytically digested and lysed papilloma virions.

EXAMPLE 7

The preparation of CMV (cytomegalovirus) DNA from urine is carried out as follows:

CMV viruses are lysed in situ upon addition of 4 M urea, 1% Triton, 500 mM NaCl, 50 mM Tris-HCl buffer, pH 7.5. The DNA (130 to 150 $\times 10^6$ Dalton) is released via adsorption on the porous matrix, concentrated in the cartridge shown in FIG. 1, and washed as described in EXAMPLE 5. Then the DNA is eluted as described in EXAMPLE 4. Since these operations are usually followed by a Dot-Blot procedure, which requires high salt concentrations to be present for binding the DNA to a membrane (nitrocellulose, nylon), the eluted DNA solution is adjusted to concentrations of 0.1 M sodium hydroxide and about 2 M sodium chloride. Then a Dot-Blot is directly possible in the devices as conventionally used, for example Minifold I and II by Schleicher & Scholl, West Germany.

EXAMPLE 8

Removal of nucleic acids from protein solutions:

To 5 ml of a BSA (bovine serum albumin) solution (1 mg/ml), there are added 50 ng of pBR 322 plasmid having tetracycline resistance (transformation equivalent about 800 colonies). The obtained solution is adjusted to 0.3 M NaCl to prevent the BSA from being bound to the chromatographic material, and then twice purified over a cartridge containing 250 mg of chromatography material (flow rate 5 ml/hour). Then the cartridge is washed with 1 M NaCl, 50 mM MOPS, pH 7.0, and the bound DNA is eluted with 1.5 M NaCl, 15% ethanol, 1 mM EDTA and 50 mM MOPS, pH 7.0, precipitated with isopropanol, and transformed into *E. coli* 800 colonies are counted. The effluent is dialyzed in a parallel operation, and then 100 $\mu$l are also transformed. No resistant colonies could be determined. A comparison of the transformation rates of the initial solution and of the eluate allows the conclusion to be drawn that approximately 100% of the DNA present is removed by using the cartridge.

EXAMPLE 9

Removal of nucleic acids from therapeutic protein preparations:

10 ml of human IgG (5mg/ml) are traced with 500 pg Eco RI linearized pBR 322 plasmid DNA (10 pg DNA/mg protein). The linearized pBR 322 are labelled with $^{32}$p to an activity of $5 \times 10^6$ counts/min.

The solution is adjusted to 0.3 M NaCl, 0.025 M Na-phosphate, pH 7.0, to prevent binding of the IgG to the chromatographic resin. The protein nucleic acid solution is pumped through a chromatography column (1 cm $\times$ 5 cm) filled with 2 g of the anion exchange resin at a flow rate of 1 ml/min. The flow through fraction is collected and the radioactivity is counted.

The column is washed with 50 ml 0.3 M NaCl, 0.025 M Na-phosphate, pH 7.0, at a flow rate of 5 ml/min. The bound nucleic acid is eluted with 1.5 M NaCl, 25 mM Na-phosphate, pH 7. The eluate fraction is collected and precipitated with 1 vol. isopropanol. The precipitated nucleic acid is dissolved in 0.3 M NaCl, 0.025 M Na-phosphate, pH 7.0, and the radioactivity is counted.

| Result: | |
|---|---|
| Starting activity: | 5,000,000 cpm |
| Flow through fraction: | 15,000 cpm |
| Wash-fraction: | 10,000 cpm |
| Eluate fraction: | 475,000 cpm |

A comparison of the radioactive fractions leads to the conclusion that with this anion exchanger >95% of the nucleic acids present in a therapeutic protein sample can be removed, reducing the nucleic acid content below 1 pg.

EXAMPLE 10

Isolation of nucleic acids from protein solutions for analysis of nucleic acid content:

The low nucleic acid content ($\leq 100$ pg/ml) of concentrated protein solutions (>2 mg/ml) causes problems in quantitative analysis of the nucleic acid content of therapeutic protein preparations. For the sensitive analysis by the dot-hybridization method, the protein has to be removed from the nucleic acid. The classical method of proteinase K digestion, phenol/chloroform extraction leads to unreproducible results and loss of nucleic acids, and prevents the quantitative analysis.

Extraction with a silica gel-based anion exchanger gives a reproducible result, with a recovery of the isolated nucleic acid without protein contamination, which is suitable for quantitive analysis.

10 mg of mouse IgG of unknown nucleic acid content are dissolved in 5 ml 0.3 M NaCl, 0.025 M Na-phosphate, pH 7.0. A cartridge (0.4 ml) filled with 200 mg silica gel-based anion exchanger is equilibrated with 0.3 M NaCl, 0.025 M Na-phosphate, pH 7.0 and the IgG solution is forced through at a flow rate of 0.5 ml/min. The cartridge is washed with 10 ml 0.3 M NaCl, 0.025 M Na-phophate, pH 7.0, at a flow rate of 2 ml/min. The bound nucleic acid is eluted with 1.5 M NaCl, 0.025 M Na-phosphate, pH 7.0, and precipitated with 0.8 vol. isopropanol. The nucleic acid is dissolved in 50 μl 1 mM Tris-HCl, pH 7.0, and the analysis is done by a dot-hybridization method with a specific mouse-cDNA clone. The efficient binding and quantitative recovery of nucleic acid under the above conditions permit the quantitive analysis of the nucleic acid content in protein solutions, even at extremely low nucleic acid contents and very high protein concentrations.

What is claimed is:

1. A method for the separation of long-chain nucleic acids from other substances in solutions containing nucleic acids and other materials, comprising:
    fixing long-chain nucleic acids in a nucleic acid-containing solution onto a porous matrix, said matrix being an anion exchanger, the porous matrix having a particle size of from about 15 to about 250 μm and a pore diameter of about 100 to 2500 nm;
    washing the porous matrix to separate the other substances from the long-chain nucleic acids; and
    removing the fixed long-chain nucleic acids from the porous matrix.

2. The method of claim 1 wherein the nucleic acid-containing solution is a nucleic acid/protein mixture or biotechnical preparation of bacteria, viruses, animal or vegetable tissue or cells, a body liquid, cell ingredients or degradation products thereof.

3. The method according to claim 1, wherein the porous matrix is selected from the group consisting of silica gel, diatomite, aluminum oxide, titanium oxide, hydroxylapatite, dextran, agarose, acrylamide, polystyrene, polyvinyl alcohol or other organic polymers, and derivatives or copolymers thereof.

4. The method according to claim 1, wherein the porous matrix is a material for chromatography having been modified with respect to its surface, the material being based on a member selected from the group consisting of silica gel, diatomite, aluminum oxide, titanium oxide, hydroxylapatite, dextran, agarose, acrylamide, polystyrene, polyvinyl alcohol or other organic polymers, and derivatives or copolymers thereof.

5. The method according to claim 1, wherein the particle size is from about 25 to about 40 μm and the pore diameter is about 400 nm.

6. The method according to claim 1, wherein the nucleic acid-containing solution is essentially phenol-free.

7. The method according to claim 1, wherein the porous matrix has a hydrophilic surface.

8. The method according to claim 1, further comprising, before the step of fixing, the step of disintegrating cells from tissue or body liquid under mild conditions by means of enzymatic proteolysis, detergents, or mechanical procedures, to obtain the nucleic acid-containing solution.

9. The method according to claim 1, wherein the step of washing uses a washing solution of low ionic strength.

10. The method according to claim 1, wherein the step of removing is performed using a solution of high ionic strength.

11. The method according to claim 1, wherein the fixed long-chain nucleic acids are separated from protein in an amount of more than 99%.

12. The method according to claim 1, wherein the fixed long-chain nucleic acids are separated from protein in an amount of up to 100%.

13. The method according to claim 1, wherein the steps of fixing, washing and removing are carried out by a batch process.

14. The method according to claim 4, wherein the porous matrix modified with respect to its surface is modified with a silanating reagent.

15. The method according to claim 1, wherein the steps of fixing, washing and removing are carried out by gravity flow of fluids applied to the matrix.

16. The method of claim 1 wherein the nucleic acid is double stranded DNA, and said DNA is removed from the porous matrix with an elution buffer comprising 1.2 M NaCl.

17. The method of claim 1 wherein the nucleic acid is single stranded DNA, and said DNA is removed from the porous matrix with an elution buffer comprising 1.1 M NaCl.

18. The method of claim 1 wherein the nucleic acid is removed from the porous matrics with an elution buffer comprising 1.5 M NaCl.

19. The method of claim 1 wherein the nucleic acid is transfer RNA, and said RNA is removed from the porous matrix with an elution buffer comprising 0.5 M NaCl.

20. The method of claim 1 wherein the nucleic acid is 5S ribosomal RNA, and said RNA is removed from the porous matrix with an elution buffer comprising 0.65 M NaCl.

21. The method of claim 1 wherein the nucleic acid is 16S and 23S ribosomal RNA or messenger RNA, and said RNA is removed from the porous matrix with an elution buffer comprising 0.8 to 0.9 M NaCl.

* * * * *